US010796449B2

(12) United States Patent
Terashima et al.

(10) Patent No.: US 10,796,449 B2
(45) Date of Patent: Oct. 6, 2020

(54) MEASUREMENT DEVICE, MEASUREMENT METHOD, AND COMPUTER READABLE RECORDING MEDIUM (71) Applicant: NEC Solution Innovators, Ltd., Tokyo (JP)

(72) Inventors: Hiroki Terashima, Tokyo (JP); Katsuyuki Nagai, Tokyo (JP); Tomomi Kinoshita, Tokyo (JP)

(73) Assignee: NEC Solution Innovators, Ltd., Koto-ku, Tokyo (JP)

( * ) Notice: Subject to any disclaimer, the term of this patent is extended or adjusted under 35 U.S.C. 154(b) by 116 days.

(21) Appl. No.: 16/084,497

(22) PCT Filed: Mar. 27, 2017

(86) PCT No.: PCT/JP2017/012462
§ 371 (c)(1),
(2) Date: Sep. 12, 2018

(87) PCT Pub. No.: WO2017/170440
PCT Pub. Date: Oct. 5, 2017

(65) Prior Publication Data
US 2019/0080472 A1 Mar. 14, 2019

(30) Foreign Application Priority Data
Mar. 28, 2016 (JP) ................. 2016-064212

(51) Int. Cl.
G06T 7/73 (2017.01)
G01B 11/00 (2006.01)
(Continued)

(52) U.S. Cl.
CPC ............... G06T 7/74 (2017.01); A61B 5/112 (2013.01); A61B 5/1128 (2013.01); G01B 11/00 (2013.01);
(Continued)

(58) Field of Classification Search
CPC .......... G06T 7/74; G06T 7/215; G06T 7/251; G06T 7/254; G06T 7/66; G06T 7/70;
(Continued)

(56) References Cited

U.S. PATENT DOCUMENTS

2012/0130280 A1   5/2012  Lee
2014/0045593 A1   2/2014  Giusti et al.
(Continued)

FOREIGN PATENT DOCUMENTS

CN   1561908 A    1/2005
CN   101515374 A  8/2009
(Continued)

OTHER PUBLICATIONS

Communication dated Oct. 30, 2019, from The China National Intellectual Property Administration in counterpart Application No. 201780017273.9.
(Continued)

Primary Examiner — Diane D Mizrahi
(74) Attorney, Agent, or Firm — Sughrue Mion, PLLC (57) ABSTRACT To measure the position of a walking user's toe tip, a measurement device includes: a data acquisition unit that acquires, from a depth sensor capturing an image of a walking path and outputting image data having a depth of each pixel added thereto, image data in which no user is on the path as reference data and image data in which a user is walking on the path as walking data; a specific pixel extraction unit that identifies a depth-sensor side foot based on the walking data and reference data and extracts, based on the depth, a pixel corresponding to a toe-tip among the pixels of the specified foot; and a position calculation unit that calculates three-dimensional coordinates of the extracted pixel based on the coordinates in the image data
(Continued)

and the depth of the pixel, and takes the three-dimensional coordinates as the position of the user's toe tip.

9 Claims, 6 Drawing Sheets

(51) Int. Cl.
    *A61B 5/11*     (2006.01)
    *G06K 9/00*     (2006.01)
    *G06T 7/20*     (2017.01)
    *A61B 5/00*     (2006.01)

(52) U.S. Cl.
    CPC ............ *G06K 9/00362* (2013.01); *G06T 7/20* (2013.01); *A61B 5/004* (2013.01); *A61B 5/0037* (2013.01); *G06T 2207/10028* (2013.01); *G06T 2207/30196* (2013.01)

(58) Field of Classification Search
    CPC ..... A61B 5/1128; A61B 5/0037; A61B 5/004; A61B 5/1116; A61B 5/112; A61B 5/165
    See application file for complete search history.

(56) References Cited

U.S. PATENT DOCUMENTS

| | | | |
|---|---|---|---|
| 2014/0243686 A1 | 8/2014 | Kimmel | |
| 2015/0077775 A1 | 3/2015 | Ogata | |
| 2015/0325004 A1 | 11/2015 | Utsunomiya et al. | |
| 2018/0222051 A1* | 8/2018 | Vu | B25J 9/1676 |
| 2018/0222052 A1* | 8/2018 | Vu | B25J 9/1666 |
| 2018/0322337 A1* | 11/2018 | Marty | G06K 9/00342 |
| 2019/0087965 A1* | 3/2019 | Datta | G06T 7/254 |

FOREIGN PATENT DOCUMENTS

| | | |
|---|---|---|
| CN | 101650776 A | 2/2010 |
| CN | 102178530 A | 9/2011 |
| CN | 102971766 A | 3/2013 |
| CN | 103971409 A | 8/2014 |
| CN | 104274179 A | 1/2015 |
| JP | 2004-28635 A | 1/2004 |
| JP | 2015-42241 A | 3/2015 |
| JP | 2015-61211 A | 3/2015 |
| KR | 10-2016-0000339 A | 1/2016 |
| WO | 2014/111708 A1 | 7/2014 |
| WO | 2016/031313 A1 | 3/2016 |

OTHER PUBLICATIONS

Lu Chen, "The Study and Implementation of Image-based Non-contacting Automatic Body Measurement System", Oct. 15, 2009, pp. 1-84 (84 pages total).

Communication dated Oct. 17, 2019, from the European Patent Office in counterpart European Application No. 17774977.7.

Naofumi Kitsunezaki et al., "KINECT application for the physical rehabilitation", The Institute of Electronics, Information and Communication Engineers, IEICE Technical Report 1E2012-89, Nov. 2012, pp. 41-46.

Satoshi Nishizawa et al., "Foot Clearance During Walking of Older Adults in the Community", Society of Biomechanisms Japan, Nov. 25, 1998, pp. 69-79, vol. 14.

International Search Report for PCT/JP2017/012462 dated Jun. 6, 2017 (PCT/ISA/210).

* cited by examiner

MEASUREMENT DEVICE, MEASUREMENT METHOD, AND COMPUTER READABLE RECORDING MEDIUM

CROSS REFERENCE TO RELATED APPLICATIONS

This application is a National Stage of International Application No. PCT/JP2017/012462 filed Mar. 27, 2017, claiming priority based on Japanese Patent Application No. 2016-064212, filed Mar. 28, 2016, the entire contents of which are hereby incorporated by reference.

TECHNICAL FIELD

The present invention relates to a measurement device and a measurement method for measuring the position of a toe tip of a walking user, and to a computer readable recording medium in which is recorded a program for realizing the measurement device and measurement method.

BACKGROUND ART

Recently, research into what is known as "foot clearance", which is the distance between a toe tip and a ground surface while walking, is garnering attention. Based on the hypothesis that as a person ages, foot clearance becomes lower and the person will experience more falls while walking, this research attempts to understand the physical condition of elderly people by measuring the foot clearance (see Non Patent Document 1, for example).

To measure the foot clearance, Non Patent Document 1 describes attaching markers to 13 locations on a subject, including the subject's heel and toe tip, and then having the subject walk. Images of the walking subject are captured using six cameras, and the foot clearance is measured on the basis of the trajectories of the markers, extracted from the captured images.

However, a high cost, a heavy physical burden on the subject, and a heavy burden on the measurer for carrying out the measurement task can be given as problems with foot clearance measurement employing this method. This is making it difficult for foot clearance measurement to become widespread. What is needed, therefore, is means for measuring foot clearance inexpensively and easily.

Recent years have seen attempts to analyze human movement using depth sensors such as Kinect (registered trademark) (see Non Patent Document 2, for example). Specifically, Non Patent Document 2 discloses a system in which images of a rehabilitating patient moving his/her joints are captured using a depth sensor to measure the range of movement of the patient's joints. The system disclosed in Non Patent Document 2 can detect each part of the patient using only image data from the depth sensor. It is therefore conceivable that foot clearance can be measured inexpensively and easily using the system disclosed in Non Patent Document 2.

LIST OF PRIOR ART DOCUMENTS

Non Patent Document

Non Patent Document 1: Nishizawa, S., Nagasaki, H., Furuna, T., Okuzumi, H., Sugiura, M., Ito, H. and Fujita, M. "Foot clearance during walking of older adults in the community." Society of Biomechanisms Japan. Vol. 14; Nov. 25, 1998; p. 69-79

Non Patent Document 2: Kitsunezaki, N., Adachi, E., Yokota, T., and Mizusawa, J. "KINECT applications for the physical rehabilitation." The Institute of Electronics, Information and Communication Engineers, IEICE technical report IE2012-89; November 2012; p. 41-46.

DISCLOSURE OF THE INVENTION

Problems to be Solved by the Invention

However, the leg joints normally identified by a depth sensor include the knee and the ankle, and even the system disclosed in Non Patent Document 2 does not include the toe tip. Thus with the system disclosed in Non Patent Document 2, it is difficult to acquire the position of the toe tip, which in turn makes it difficult to actually measure the foot clearance.

One example of an object of the present invention is to provide a measurement device, a measurement method, and a computer readable recording medium that can make it possible to measure foot clearance using a depth sensor.

Means for Solving the Problems

To solve the above-described problems, a measurement device according to one aspect of the present invention is a device for measuring the position of a toe tip of a walking user, the device including:
  a data acquisition unit that acquires, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;
  a specific pixel extraction unit that finds a difference between the walking data and the reference data, identifies a leg of the user located on the depth sensor side from the difference that has been found and a depth included in the difference, and furthermore extracts, from pixels constituting the identified leg, a pixel of a toe tip part on the basis of the depth; and
  a position calculation unit that calculates three-dimensional coordinates of the pixel from coordinates of the extracted pixel in the image data and the depth of the extracted pixel, and takes the calculated three-dimensional coordinates as the position of the toe tip of the user.

Additionally, to solve the above-described problems, a measurement method according to one aspect of the present invention is a method for measuring the position of a toe tip of a walking user, the method including:
  (a) a step of acquiring, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;
  (b) a step of finding a difference between the walking data and the reference data, identifying a leg of the user located on the depth sensor side from the difference that has been found and a depth included in the difference, and furthermore extracting, from pixels constituting the identified leg, a pixel of a toe tip part on the basis of the depth; and
  (c) a step of calculating three-dimensional coordinates of the pixel from coordinates of the extracted pixel in the image data and the depth of the extracted pixel, and taking the calculated three-dimensional coordinates as the position of the toe tip of the user.

Additionally, to solve the above-described problems, a computer readable recording medium according to one aspect of the present invention is a computer readable recording medium storing a program for measuring the position of a toe tip of a walking user using a computer, the program including commands that cause the computer to execute:

(a) a step of acquiring, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;

(b) a step of finding a difference between the walking data and the reference data, identifying a leg of the user located on the depth sensor side from the difference that has been found and a depth included in the difference, and furthermore extracting, from pixels constituting the identified leg, a pixel of a toe tip part on the basis of the depth; and (c) a step of calculating three-dimensional coordinates of the pixel from coordinates of the extracted pixel in the image data and the depth of the extracted pixel, and taking the calculated three-dimensional coordinates as the position of the toe tip of the user.

Advantageous Effects of the Invention

According to the present invention as described above, foot clearance can be measured using a depth sensor.

BRIEF DESCRIPTION OF THE DRAWINGS

FIGS. 3(a)-3(c) are diagrams illustrating an example of image data output from a depth sensor according to the embodiment of the present invention, where FIG. 3(a) illustrates a state where no user is present in a walking path, FIG. 3(b) illustrates a state where a user is present in the walking path, and FIG. 3(c) illustrates a difference.

FIGS. 4(a)-4(b) are diagrams illustrating a process of calculating three-dimensional coordinates according to the embodiment of the present invention, where FIG. 4(a) illustrates a horizontal direction of a screen and FIG. 4(b) illustrates a vertical direction of the screen.

MODE FOR CARRYING OUT THE INVENTION

Embodiment

A measurement device, a measurement method, and a program according to an embodiment of the present invention will be described hereinafter with reference to FIGS. 1 to 5.

[Device Configuration]

Figure 1:
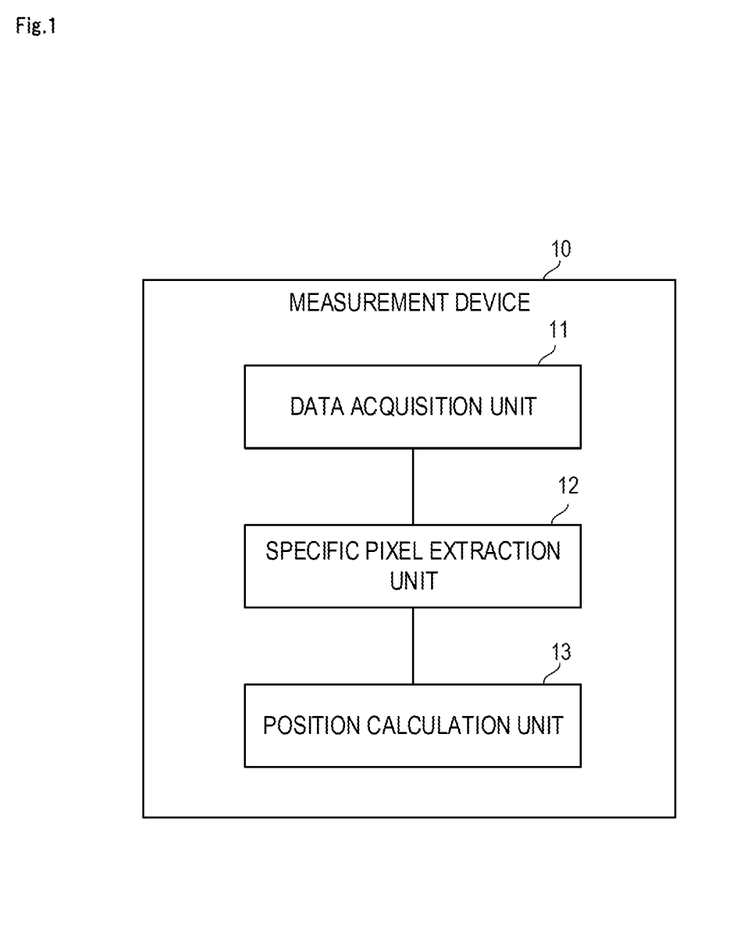
FIG. 1 is a block diagram illustrating the overall configuration of a measurement device according to an embodiment of the present invention.

First, the overall configuration of the measurement device according to the present embodiment will be described using FIG. 1. FIG. 1 is a block diagram illustrating the overall configuration of the measurement device according to the embodiment of the present invention.

A measurement device 10 according to the present embodiment, illustrated in FIG. 1, is a device that measures the position of a walking user's toe tip. As illustrated in FIG. 1, the measurement device 10 includes a data acquisition unit 11, a specific pixel extraction unit 12, and a position calculation unit 13.

The data acquisition unit 11 first acquires, from a depth sensor, image data of a state in which a user is not present in a walking path, as reference data (see FIG. 3(a), described later). Furthermore, the data acquisition unit 11 acquires, from the depth sensor, image data of a state in which the user is walking in the walking path, as walking data (see FIG. 3(b), described later). The depth sensor is arranged so as to capture a pre-set walking path and a space above the walking path. The depth sensor outputs the image data with a depth added to each pixel.

The specific pixel extraction unit 12 finds a difference between the walking data and the reference data, and identifies the leg of the user located on the depth sensor side, from the difference that has been found (see FIG. 3(c), described later) and the depths included in that difference. The specific pixel extraction unit 12 then extracts a pixel of a toe tip part from the pixels constituting the identified leg, on the basis of the depth. The position calculation unit 13 calculates three-dimensional coordinates of the pixel from the coordinates of the extracted pixel in the image data and the depth of the extracted pixel, and takes the calculated three-dimensional coordinates as the position of the user's toe tip.

Thus in the present embodiment, the measurement device 10 can identify the position of the toe tip by using the image data from the depth sensor, to which the depths have been added. As such, according to the present embodiment, foot clearance can be measured using the depth sensor.

Figure 2:
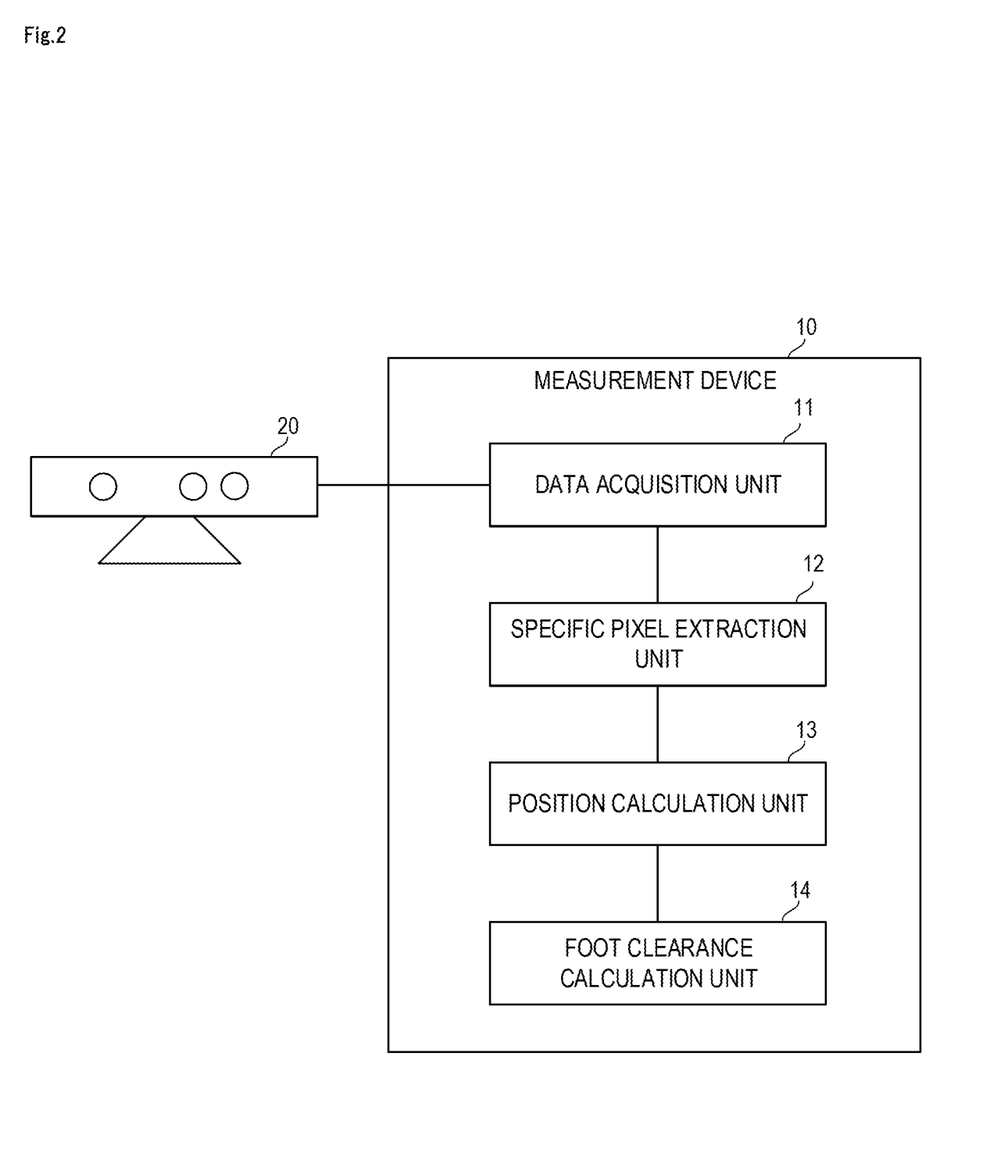
FIG. 2 is a block diagram illustrating the detailed configuration of the measurement device according to the embodiment of the present invention.

Next, the detailed configuration of the measurement device according to the present embodiment will be described using FIGS. 2 and 3. FIG. 2 is a block diagram illustrating the detailed configuration of the measurement device according to the embodiment of the present invention. FIG. 3 is a diagram illustrating an example of the image data output from the depth sensor according to the embodiment of the present invention, where FIG. 3(a) illustrates a state where no user is present in the walking path, FIG. 3(b) illustrates a state where a user is present in the walking path, and FIG. 3(c) illustrates a difference.

As illustrated in FIG. 2, in the present embodiment, the measurement device 10 is connected to a depth sensor 20. The measurement device 10 receives the image data, to which a depth is added to each pixel, from the depth sensor 20 over a wire or wirelessly. The depth sensor 20 includes, for example, a light source that emits infrared laser light in a specific pattern and an image sensor that receives the infrared light after being reflected by an object, thereby outputting the image data to which a depth is added to each pixel. An existing depth sensor such as Kinect (registered trademark) can be given as a specific example of the depth sensor.

Figure 3A:
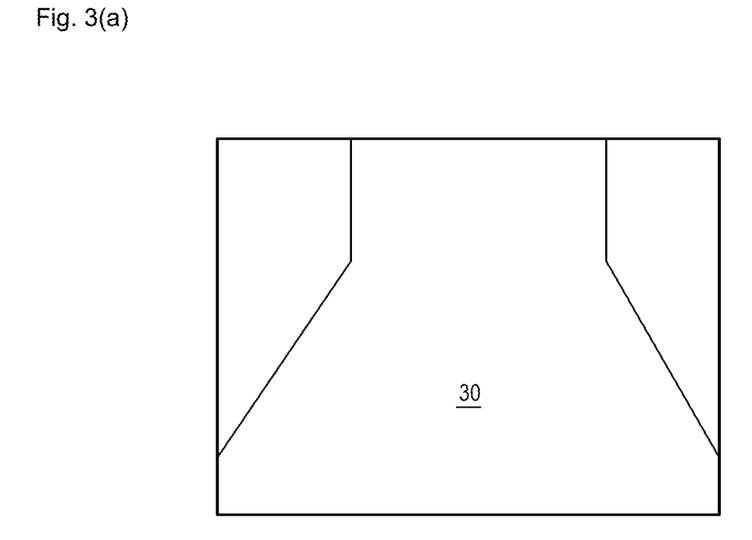
Figure 3B:
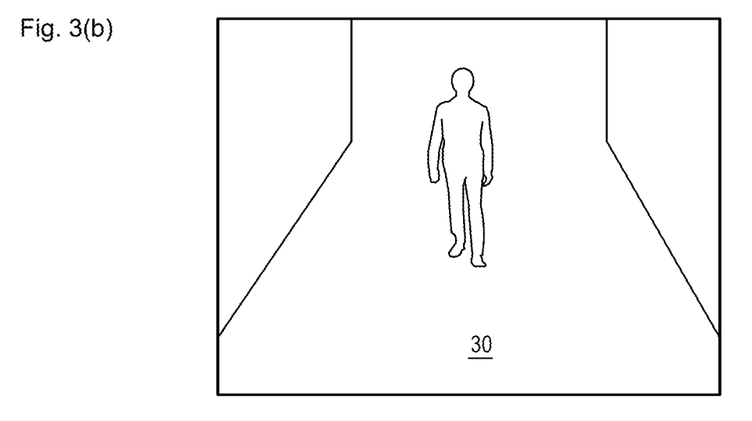
Figure 3C:
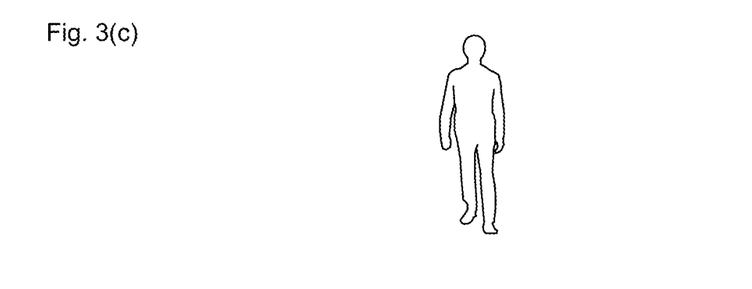

Additionally, as illustrated in FIGS. 3(a) and 3(b), the depth sensor 20 is arranged so as to be capable of capturing images of a walking path 30 and the space thereabove. The walking path 30 may be any planar location on which a user can walk, and is not particularly limited.

As illustrated in FIG. 2, in the present embodiment, the measurement device 10 includes a foot clearance calculation unit 14 in addition to the data acquisition unit 11, the specific pixel extraction unit 12, and the position calculation unit 13.

In the present embodiment, each time the walking data is obtained, the specific pixel extraction unit 12 identifies a plurality of parts of the four limbs and trunk of the user in image data corresponding to a difference between the walking data and the reference data (called "difference image data" hereinafter; see FIG. 3(c)). The specific pixel extraction unit 12 furthermore identifies coordinates and a depth, in the image data, of each of the identified parts, and calculates three-dimensional coordinates of each part using the coordinates and depth.

Note that in the present specification, the three-dimensional coordinates are constituted by the coordinates of the pixel in the image data and the depth added to the pixel. The identified part is the head, the neck, the right shoulder, the right elbow, the right wrist, the thumb of the right hand, the tip of the right hand, the left shoulder, the left elbow, the left wrist, the thumb of the left hand, the tip of the left hand, the chest, the lower back, the pelvis, the right hip joint, the right knee, the right ankle, the top of the right foot, the left hip joint, the left knee, the left ankle, and the top of the left foot.

Figure 4A:
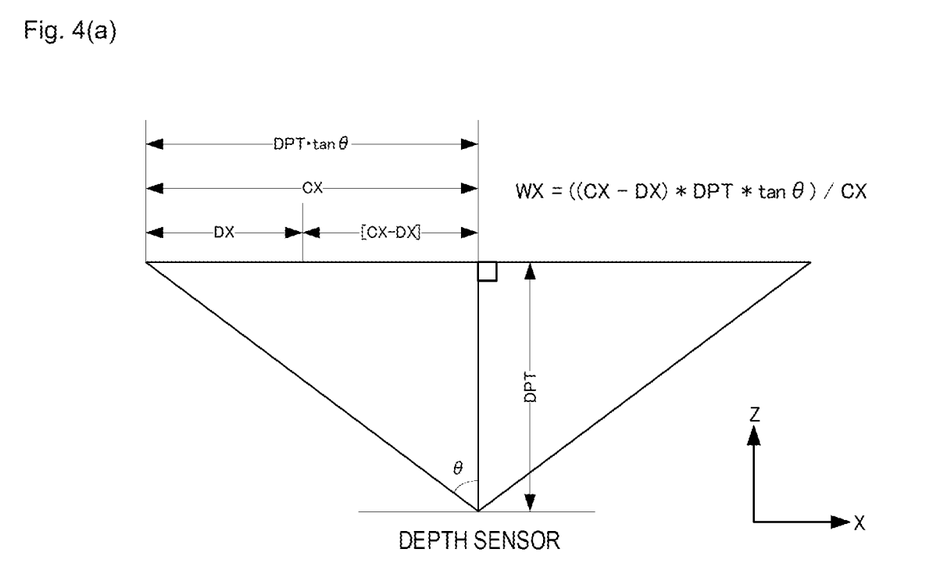
Figure 4B:
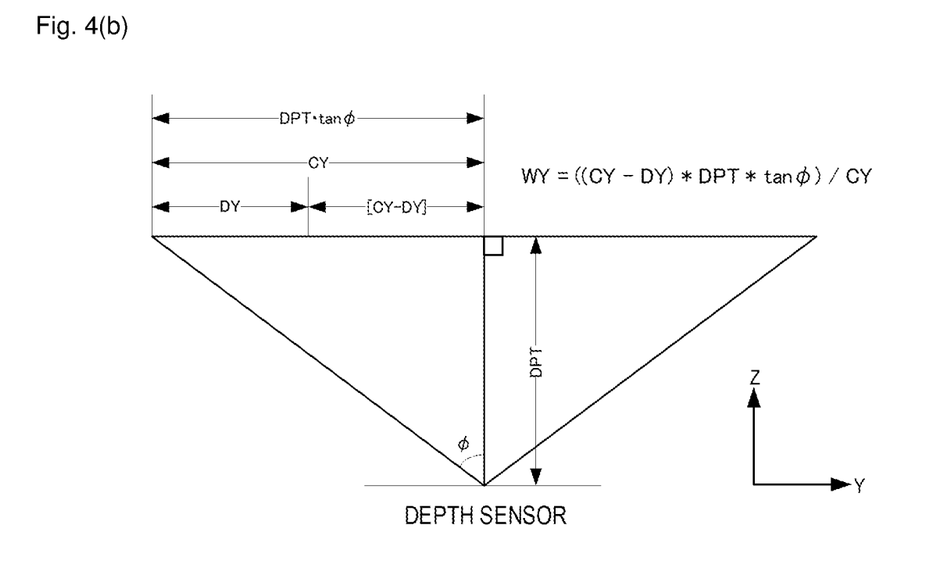

The method for calculating the three-dimensional coordinates from the coordinates and depth in the image data is as follows. FIG. 4 is a diagram illustrating a process of calculating the three-dimensional coordinates according to the embodiment of the present invention, where FIG. 4(a) illustrates an X-Z plane in a three-dimensional space and FIG. 4(b) illustrates a Y-Z plane in the three-dimensional space.

First, the coordinates of a specific point in the image data to which a depth has been added are represented by (DX, DY), and the depth at the specific point is represented by DPT. The number of pixels in the image data in the horizontal direction is represented by 2CX, and the number of pixels in the vertical direction is represented by 2CY. An angle of view of the depth sensor in the horizontal direction is represented by 2θ, and an angle of view in the vertical direction is represented by 2φ. In this case, three-dimensional coordinates (WX,WY,WZ) of the specific point can be calculated through the following Equations 1 to 3, as can be seen from FIGS. 4(a) and (b).

$$WX=((CX-DX) \times DPT \times \tan\theta)/CX \qquad \text{Equation 1}$$

$$WY=((CY-DY) \times DPT \times \tan\varphi)/CY \qquad \text{Equation 2}$$

$$WZ=DPT \qquad \text{Equation 3}$$

Then, using the three-dimensional coordinates of the positions of the left and right ankles, the specific pixel extraction unit 12 compares the depth of the right ankle with the depth of the left ankle, and specifies the leg having the lower value as the leg closer to the depth sensor (FIGS. 3(a) and (b)).

For the specified leg, the specific pixel extraction unit 12 takes the midpoint of a line segment connecting the knee to the ankle in the three-dimensional space as the shin, and calculates three-dimensional coordinates of the shin from the three-dimensional coordinates of the knee and the three-dimensional coordinates of the ankle. Furthermore, the specific pixel extraction unit 12 calculates the coordinates of the shin in the image data from the calculated three-dimensional coordinates of the shin, and on the basis of the calculated coordinates, extracts a part lower than the user's shin from the pixels constituting the region of the specified leg. Then, on the basis of the depths of the pixels constituting the extracted part, the specific pixel extraction unit 12 furthermore extracts the pixels, among the pixels constituting the extracted part, that are located the furthest forward, i.e., that have the smallest depths, and takes the extracted pixels as the pixels of the toe tip part.

In the present embodiment, the position calculation unit 13 first calculates the coordinates, in the original image data, of the pixels extracted by the specific pixel extraction unit 12 as the pixels of the toe tip part. The position calculation unit 13 calculates the three-dimensional coordinates of the user's toe tip using the calculated coordinates in the image data and the depths of the extracted pixels.

The foot clearance calculation unit 14 repeatedly acquires the three-dimensional coordinates of the user's toe tip calculated by the position calculation unit 13, and each time the three-dimensional coordinates are acquired, calculates the foot clearance by comparing the acquired three-dimensional coordinates with the three-dimensional coordinates of the walking path 30, which are registered in advance. Specifically, the foot clearance is calculated by calculating a difference between vertical direction components of the two sets of three-dimensional coordinates, for example. The calculated foot clearance is displayed in the screen of a display device or the like connected to the measurement device 10 along with the right leg and left leg determination results, for example. Thus according to the measurement device 10, the foot clearance can be measured with a simple system configuration.

[Device Operations]

Figure 5:
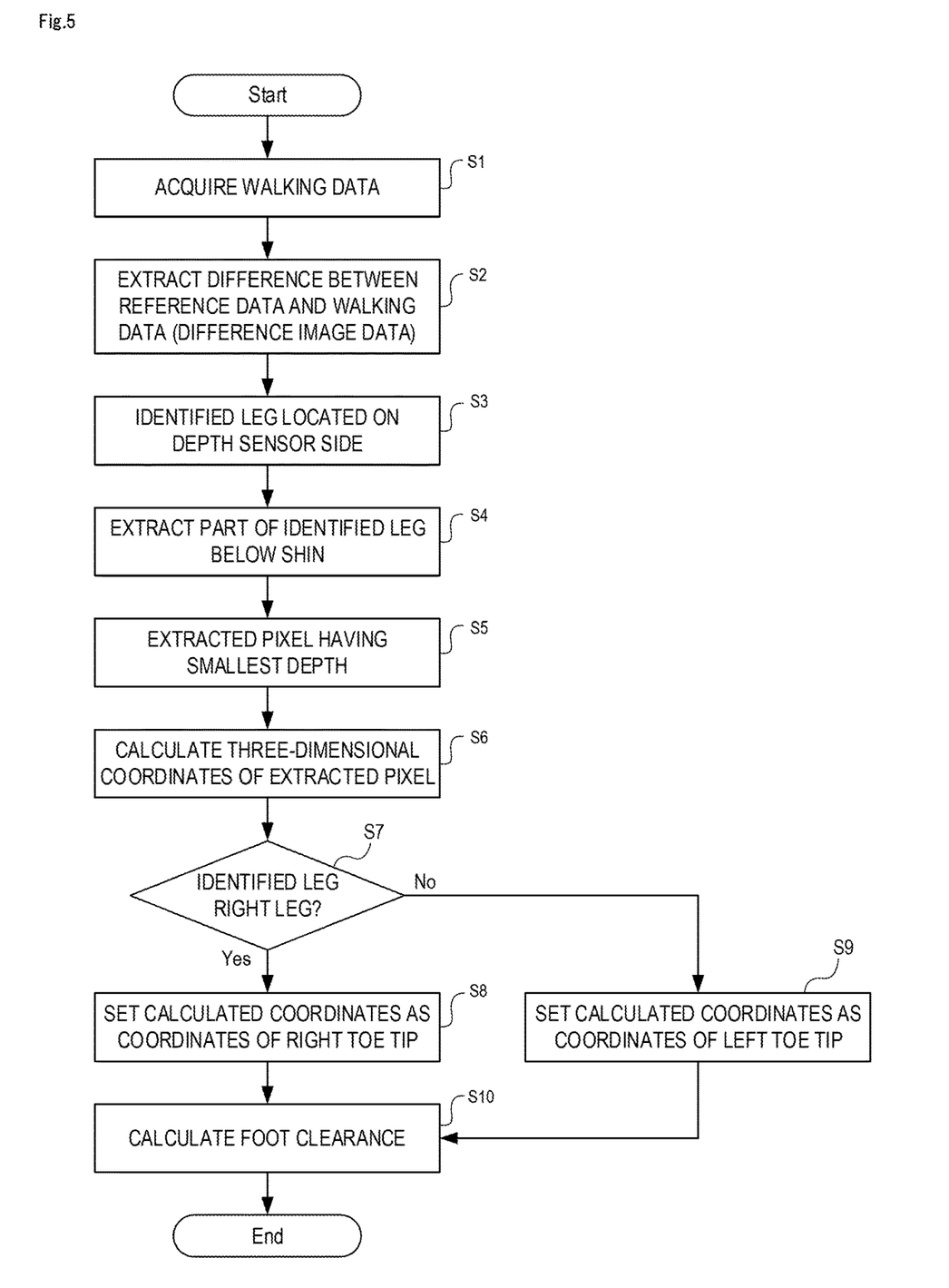
FIG. 5 is a flowchart illustrating operations of the measurement device according to the embodiment of the present invention.

Next, operations of the measurement device 10 according to the embodiment of the present invention will be described using FIG. 5. FIG. 5 is a flowchart illustrating operations of the measurement device 10 according to the embodiment of the present invention. The following descriptions will refer to FIGS. 1 to 4 as appropriate. In the present embodiment, the measurement method is realized by causing the measurement device 10 to operate. The following descriptions of the operations of the measurement device 10 will be given in place of descriptions of the measurement method according to the present embodiment.

First, it is assumed that the data acquisition unit 11 has acquired the reference data from the depth sensor 20 in advance. Then, as illustrated in FIG. 3(b), the depth sensor 20 captures the user walking along the walking path 30, and when the acquired image data is output, the data acquisition unit 11 acquires the walking data (step S1).

Next, the specific pixel extraction unit 12 finds the image data indicating the difference between the walking data obtained in step S1 and the reference data (the difference image data), and extracts the difference image data (step S2).

Then, the specific pixel extraction unit 12 identifies a plurality of parts of the four limbs and trunk of the user in the difference image data extracted in step S2, and calculates the three-dimensional coordinates of the identified parts. Then, using the three-dimensional coordinates of the positions of the left and right ankles, the specific pixel extraction unit 12 compares the depth of the right ankle with the depth of the left ankle, and specifies the leg of the user located closer to the depth sensor (step S3).

Next, the specific pixel extraction unit 12 extracts the part lower than the user's shin from the pixels constituting the leg specified in step S3 (step S4).

Next, on the basis of the depths of the pixels constituting the extracted part, the specific pixel extraction unit 12 further extracts the pixels, among the pixels constituting the extracted part, that have the smallest depths (step S5). These extracted pixels correspond to the pixels of the toe tip part.

Next, the position calculation unit 13 calculates the coordinates, in the original image data, of the pixels extracted in step S5, and then calculates the three-dimensional coordinates of the pixels extracted in step S5 from the calculated coordinates in the image data and the depths of the pixels extracted in step S5 (step S6). The calculated three-dimensional coordinates indicate the position of the user's toe tip.

Next, the position calculation unit 13 determines whether or not the leg identified in step S3 is the user's right leg (step S7). If the result of the determination in step S7 indicates that the leg is the right leg, the position calculation unit 13 takes the coordinates calculated in step S6 as the coordinates of the right toe tip (step S8). However, if the result of the determination in step S7 indicates that the leg is not the right leg, the position calculation unit 13 takes the coordinates calculated in step S6 as the coordinates of the left toe tip (step S9).

After step S8 or S9 has been executed, the foot clearance calculation unit 14 calculates the foot clearance by comparing the three-dimensional coordinates calculated in step S6 with the three-dimensional coordinates of the walking path 30 registered in advance (step S10). In step S10, the foot clearance calculation unit 14 displays the calculated foot clearance and the right leg/left leg determination result in a screen of a display device or the like connected to the measurement device 10.

The above-described steps S1 to S10 are executed repeatedly, each time the depth sensor 20 captures the user walking along the walking path 30 and the acquired image data is output, i.e., for each frame.

Effects of Embodiment

Thus according to the measurement device 10, the position of the toe tip can be identified, and the foot clearance can be measured accurately, simply by the depth sensor 20 capturing the user in a state of walking. Additionally, according to the measurement device 10, a simple system configuration is sufficient, which suppresses an increase in the costs required to measure the foot clearance.

[Program]

A program according to the present embodiment may be any program that causes a computer to execute steps S1 to S10 illustrated in FIG. 5. The measurement method and the measurement device 10 according to the present embodiment can be realized by installing the program in a computer and executing the program. In this case, a CPU (Central Processing Unit) of the computer carries out the processing by functioning as the data acquisition unit 11, the specific pixel extraction unit 12, the position calculation unit 13, and the foot clearance calculation unit 14.

The program according to the present embodiment may be executed by a computer system constructed from a plurality of computers. In this case, for example, each computer may function as any of the data acquisition unit 11, the specific pixel extraction unit 12, the position calculation unit 13, and the foot clearance calculation unit 14.

Figure 6:
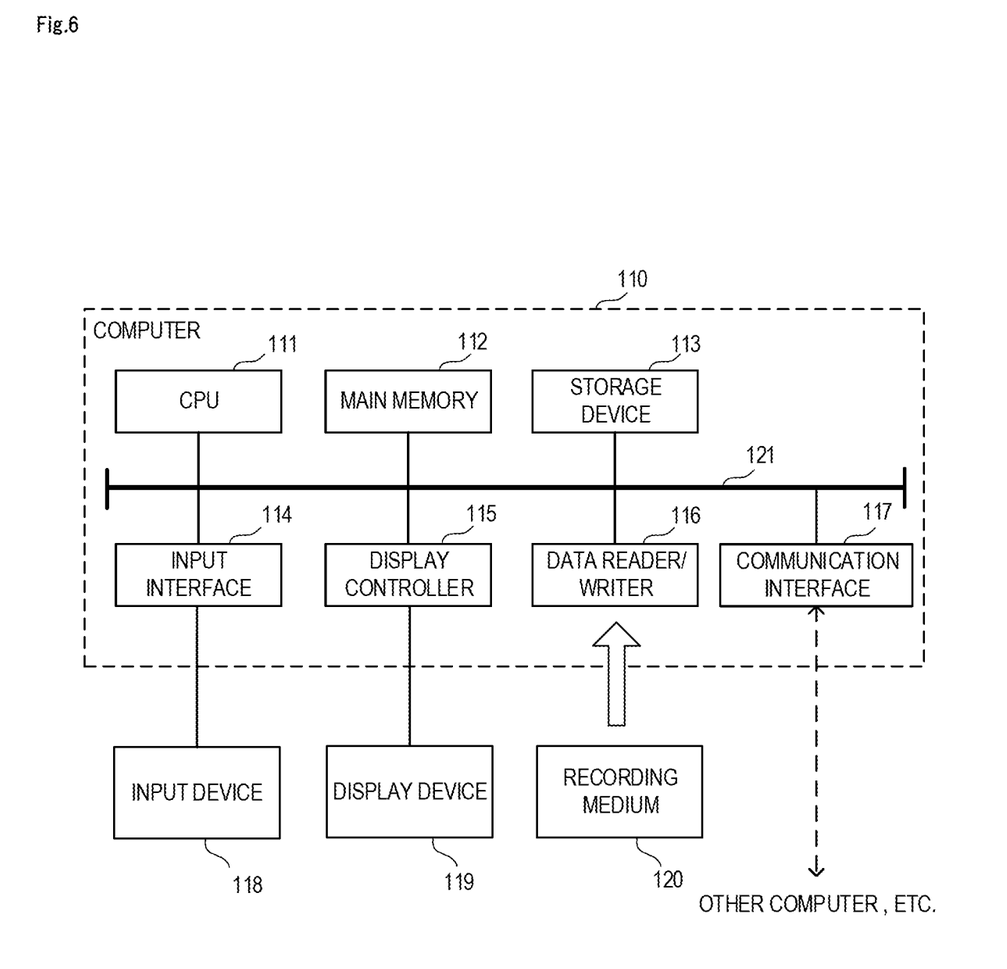
FIG. 6 is a block diagram illustrating an example of a computer realizing the measurement device according to the embodiment of the present invention.

A computer that realizes the measurement device 10 by executing the program according to the present embodiment will be described using FIG. 6. FIG. 6 is a block diagram illustrating an example of a computer realizing the measurement device according to the embodiment of the present invention.

As illustrated in FIG. 6, a computer 110 includes a CPU 111, main memory 112, a storage device 113, an input interface 114, a display controller 115, a data reader/writer 116, and a communication interface 117. These units are connected by a bus 121 so as to be capable of data communication with each other.

The CPU 111 loads the program (code) according to the present embodiment, which is stored in the storage device 113, into the main memory 112, and executes the program according to a prescribed sequence, thereby carrying out various types of operations. The main memory 112 is typically a volatile storage device such as DRAM (Dynamic Random Access Memory) or the like. The program according to the present embodiment is stored in a computer readable recording medium 120 and provided in such a state. Note that the program according to the present embodiment may be distributed over the Internet, which is connected via the communication interface 117.

In addition to a hard disk drive, a semiconductor storage device such as flash memory or the like can be given as a specific example of the storage device 113. The input interface 114 facilitates data transfer between the CPU 111 and an input device 118 such as a keyboard and a mouse. The display controller 115 can be connected to a display device 119, and controls displays made in the display device 119.

The data reader/writer 116 facilitates data transfer between the CPU 111 and the recording medium 120, reads out programs from the recording medium 120, and writes results of processing performed by the computer 110 into the recording medium 120. The communication interface 117 facilitates data exchange between the CPU 111 and other computers.

A generic semiconductor storage device such as CF (Compact Flash (registered trademark)), SD (Secure Digital), or the like, a magnetic storage medium such as a flexible disk or the like, an optical storage medium such as a CD-ROM (Compact Disk Read Only Memory) or the like, and so on can be given as specific examples of the recording medium 120.

Note that the measurement device 10 according to the present embodiment can also be realized using hardware corresponding to the respective units, instead of a computer in which a program is installed. Furthermore, the measurement device 10 may be partially realized by a program, with the remaining parts realized by hardware.

All or part of the above-described embodiment can be expressed as Addendum 1 to Addendum 9, described hereinafter, but is not intended to be limited to the following descriptions.

(Addendum 1)

A device for measuring a position of a toe tip of a walking user, the device comprising:

a data acquisition unit that acquires, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;

a specific pixel extraction unit that finds a difference between the walking data and the reference data, identifies a leg of the user located on the depth sensor side from the difference that has been found and a depth included in the difference, and furthermore extracts, from pixels constituting the identified leg, a pixel of a toe tip part on the basis of the depth; and a position calculation unit that calculates three-dimensional coordinates of the pixel from coordinates of the extracted pixel in the image data and the depth of the extracted pixel, and takes the calculated three-dimensional coordinates as the position of the toe tip of the user.

(Addendum 2)

The measurement device according to Addendum 1, wherein the position calculation unit determines whether the identified leg is a right leg or a left leg of the user, and takes the calculated position of the toe tip of the user as the position of a toe tip of the leg on the side that has been determined.

(Addendum 3)

The measurement device according to Addendum 1 or 2, wherein the specific pixel extraction unit extracts a pixel, among pixels constituting the identified leg, having the smallest depth.

(Addendum 4)

A method for measuring a position of a toe tip of a walking user, the method comprising:

(a) a step of acquiring, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;

(b) a step of finding a difference between the walking data and the reference data, identifying a leg of the user located on the depth sensor side from the difference that has been found and a depth included in the difference, and furthermore extracting, from pixels constituting the identified leg, a pixel of a toe tip part on the basis of the depth; and (c) a step of calculating three-dimensional coordinates of the pixel from coordinates of the extracted pixel in the image data and the depth of the extracted pixel, and taking the calculated three-dimensional coordinates as the position of the toe tip of the user.

(Addendum 5)

The measurement method according to Addendum 4, further comprising:

(d) a step of determining whether the identified leg is a right leg or a left leg of the user, and taking the calculated position of the toe tip of the user as the position of a toe tip of the leg on the side that has been determined.

(Addendum 6)

The measurement method according to Addendum 4 or 5, wherein in step (b), a pixel, among pixels constituting the identified leg, having the smallest depth is extracted.

(Addendum 7)

A computer readable recording medium storing a program for measuring the position of a toe tip of a walking user using a computer, the program including commands for causing the computer to execute:

(a) a step of acquiring, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;

(b) a step of finding a difference between the walking data and the reference data, identifying a leg of the user located on the depth sensor side from the difference that has been found and a depth included in the difference, and furthermore extracting, from pixels constituting the identified leg, a pixel of a toe tip part on the basis of the depth; and (c) a step of calculating three-dimensional coordinates of the pixel from coordinates of the extracted pixel in the image data and the depth of the extracted pixel, and taking the calculated three-dimensional coordinates as the position of the toe tip of the user.

(Addendum 8)

The computer readable recording medium according to Addendum 7, further causing the computer to execute:

(d) a step of determining whether the identified leg is a right leg or a left leg of the user, and taking the calculated position of the toe tip of the user as the position of a toe tip of the leg on the side that has been determined.

(Addendum 9)

The computer readable recording medium according to Addendum 7 or 8, wherein in step (b), a pixel, among pixels constituting the identified leg, having the smallest depth is extracted.

While the present invention has been described above with reference to embodiments, the present invention is not intended to be limited to the above embodiments. Many variations can be made, by one of ordinary skill in the art, on the configuration and details of the present invention without departing from the scope of the present invention.

INDUSTRIAL APPLICABILITY

According to the present invention as described above, foot clearance can be measured using a depth sensor. The present invention is useful in fields where there is a need to understand the physical condition of a user.

DESCRIPTION OF REFERENCE NUMERALS

10 Measurement Device
11 Data Acquisition Unit
12 Specific Pixel Extraction Unit
13 Position Calculation Unit
14 Foot Clearance Calculation Unit
20 Depth Sensor
30 Walking Path
111 CPU
112 Main Memory
113 Storage Device
114 Input Interface
115 Display Controller
116 Data Reader/Writer
117 Communication Interface
118 Input Device
119 Display Device
120 Recording Medium
121 Bus

The invention claimed is:

1. A device for measuring a position of a toe tip of a walking user, the device comprising:
a data acquisition unit that acquires, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;
a specific pixel extraction unit that finds a difference between the walking data and the reference data, identifies a leg of the user located on the depth sensor side from the difference that has been found and a depth included in the difference, and furthermore extracts, from pixels constituting the identified leg, a pixel of a toe tip part on the basis of the depth; and a position calculation unit that calculates three-dimensional coordinates of the pixel from coordinates of the extracted pixel in the image data and the depth of the extracted pixel, and takes the calculated three-dimensional coordinates as the position of the toe tip of the user.

2. The measurement device according to claim 1, wherein the position calculation unit determines whether the identified leg is a right leg or a left leg of the user, and takes the calculated position of the toe tip of the user as the position of a toe tip of the leg on the side that has been determined.

3. The measurement device according to claim 1, wherein the specific pixel extraction unit extracts a pixel, among pixels constituting the identified leg, having the smallest depth.

4. A method for measuring a position of a toe tip of a walking user, the method comprising:
  (a) a step of acquiring, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;
  (b) a step of finding a difference between the walking data and the reference data, identifying a leg of the user located on the depth sensor side from the difference that has been found and a depth included in the difference, and furthermore extracting, from pixels constituting the identified leg, a pixel of a toe tip part on the basis of the depth; and
  (c) a step of calculating three-dimensional coordinates of the pixel from coordinates of the extracted pixel in the image data and the depth of the extracted pixel, and taking the calculated three-dimensional coordinates as the position of the toe tip of the user.

5. The measurement method according to claim 4, further comprising:
  (d) a step of determining whether the identified leg is a right leg or a left leg of the user, and taking the calculated position of the toe tip of the user as the position of a toe tip of the leg on the side that has been determined.

6. The measurement method according to claim 4, wherein in step (b), a pixel, among pixels constituting the identified leg, having the smallest depth is extracted.

7. A non-transitory computer readable recording medium storing a program for measuring the position of a toe tip of a walking user using a computer, the program including commands for causing the computer to execute:
  (a) a step of acquiring, from a depth sensor disposed so as to capture an image of a walking path set in advance and a space above the walking path and outputting image data having a depth of each pixel added thereto, image data for a state in which there is no user on the walking path as reference data and image data for a state in which a user is walking on the walking path as walking data;
  (b) a step of finding a difference between the walking data and the reference data, identifying a leg of the user located on the depth sensor side from the difference that has been found and a depth included in the difference, and furthermore extracting, from pixels constituting the identified leg, a pixel of a toe tip part on the basis of the depth; and
  (c) a step of calculating three-dimensional coordinates of the pixel from coordinates of the extracted pixel in the image data and the depth of the extracted pixel, and taking the calculated three-dimensional coordinates as the position of the toe tip of the user.

8. The non-transitory computer readable recording medium according to claim 7, wherein the program further includes commands for causing the computer to execute:
  (d) a step of determining whether the identified leg is a right leg or a left leg of the user, and taking the calculated position of the toe tip of the user as the position of a toe tip of the leg on the side that has been determined.

9. The non-transitory computer readable recording medium according to claim 7, wherein in step (b), a pixel, among pixels constituting the identified leg, having the smallest depth is extracted.

* * * * *